US006682749B1

(12) United States Patent
Potechin et al.

(10) Patent No.: US 6,682,749 B1
(45) Date of Patent: Jan. 27, 2004

(54) LOW RESIDUE COSMETIC COMPOSITION

(75) Inventors: Kathy J. Potechin, Short Hills, NJ (US); Eric P. Guenin, Hopewell Township, NJ (US); Xiaozhong Tang, Piscataway, NJ (US); Jairajh Mattai, Piscataway, NJ (US); Elizabeth Linn, Lyndhurst, NJ (US); Wilson Lee, Bloomfield, NJ (US); Paul J. Vincenti, Jefferson, NJ (US)

(73) Assignee: Colgate-Palmolive Company, New York, NY (US)

( * ) Notice: Subject to any disclaimer, the term of this patent is extended or adjusted under 35 U.S.C. 154(b) by 811 days.

(21) Appl. No.: 09/273,152

(22) Filed: Mar. 19, 1999

Related U.S. Application Data

(63) Continuation-in-part of application No. 09/054,666, filed on Apr. 3, 1998, now abandoned.

(51) Int. Cl.[7] .............................. A61K 7/00; A61K 6/00; A61K 7/34; A61K 7/38; A61K 31/74
(52) U.S. Cl. .......................... 424/401; 424/66; 424/68; 424/78.03; 514/63
(58) Field of Search ............................ 424/401, 66, 68, 424/78.03; 514/63

(56) References Cited

U.S. PATENT DOCUMENTS

| 5,302,381 A | * | 4/1994 | Greczyn et al. ............... 424/66 |
| 5,654,362 A | | 8/1997 | Schulz, Jr. et al. ......... 524/862 |
| 5,871,717 A | | 2/1999 | Bretzler et al. ................ 424/65 |
| 5,880,210 A | | 3/1999 | Schulz, Jr. et al. ......... 524/731 |
| 5,919,437 A | * | 7/1999 | Lee et al. ..................... 424/68 |

* cited by examiner

Primary Examiner—Sreeni Padmanabhan
Assistant Examiner—Lauren Q. Wells
(74) Attorney, Agent, or Firm—Rosemary M. Miano

(57) ABSTRACT

This invention comprises low residue cosmetic compositions (especially underarm products) which are made by combining an active ingredient; a silicone gel material itself comprising an elastomer composition; and at least one selected surfactant having an HLB value in the range of 8–16. The compositions of this invention exhibit reduced or eliminated film formation when applied to the skin and increased availABILity of the active ingredient.

32 Claims, No Drawings

LOW RESIDUE COSMETIC COMPOSITION

This is a in-part divisional of pending prior application Ser. No. 09/054,66 filed Apr. 3, 1998 now abandoned which application is now pending and is incorporated herein by reference.

FIELD OF THE INVENTION

This invention is a continuation-in-part of U.S. Ser. No. 09/054,666, filed Apr. 3. 1998, and relates to an improved low residue cosmetic composition for use in underarm products such as antiperspirants and deodorants. The compositions of this invention use specific types of silicone elastomers and give improved properties.

BACKGROUND OF THE INVENTION

The present invention is directed to a cosmetic composition (especially a gelled composition) which leaves little or no visible (white) residue on the skin, and which has improved properties especially in the areas of glidability, skin feel, smoothness, reduction in tack, reduction in syneresis, and increased efficacy. In particular, the present invention may be used to formulate cosmetic compositions which contain at least one cosmetically active material (for example, a member selected from the group comprising antiperspirant active materials, deodorant active materials, insect repellents, antifungal agents, antimicrobials (also called bacteriostats or antibacterials), and fragrances), which leaves little or no visible residue on the skin, and which has improved aesthetic properties as described above. A particular area of emphasis is underarm products such as antiperspirant and/or deodorant compositions which utilize an antiperspirant active and/or an antimicrobial.

There is a continuing trend to develop new and superior cosmetic compositions especially for the reduction and/or elimination of wetness and/or odor under the arms. Particular efforts include developing clearer and lower residue products as well as raising the performance and aesthetics of such products. Various product forms have included sticks (especially gel/sticks), gels, soft solids, roll-ons, aerosols and creams. Of these various forms the sticks, gels, soft solids creams and roll-ons are made with a liquid base material incorporating a solidifying agent and/or gelling agent and/or thickening agent. Generally, these forms include a solution of the cosmetically active ingredient in a suitable vehicle, a suspension of the active ingredient in a carrier vehicle, or a multiphasic dispersion or emulsion in which a solution of the active ingredient is dispersed or suspended in some continuous phase or in which the solubilized active ingredient constitutes the continuous phase.

A variety of soft-solid formulations are known. These include formulations made with the following ingredients:

(a) clay thickening agent and an activator for the clay: for example, U.S. Pat. No. 5,019,375 to Tanner et al; and U.S. Pat. No. 4,526,780 to Marschner et al;

(b) particulate thickening agents such as fumed silica: for example, U.S. Pat. No. 5,069,897 to Orr; and U.S. Pat. No. 4,937,069 to Shin;

(c) selected volatile and/or non-volatile alkylmethylsiloxanes such as those including a structuring wax: for example, U.S. Pat. No. 5,225,188 to Abrutyn et al; and PCT applications WO 97/16161 and 16162 both of which are assigned to Unilever PLC; and (d) triglyceride gellants such as the glyceryl tribehenate described in U.S. Pat. No. 5,718,890 to Putnam et al.

An attempt to use silicone gel materials without the incorporation of clay or wax into the cosmetic formulations is described in PCT case WO 97/44010 and assigned to the same assignee as this application. One type of silicone gel material in this application is made by combining (a) a volatile silicone material and (b) an organopolysiloxane material (or silicone elastomer) as a gelling agent wherein the organopolysiloxane material (silicone elastomer) can be a reaction product of a vinyl-terminated siloxane polymer and a silicon hydride cross-linking agent. Related technology is also disclosed in PCT case WO 98/00097, WO 98/00104 and 98/00105 assigned to Unilever PLC on cross-linked non-emulsifying elastomers.

U.S. Pat. No. 5,599,533 to Stepniewski et al assigned to Estee Lauder describes a stable water-in-oil emulsion system formed with an organopolysiloxane elastomer, a vehicle in which the elastomer is dispersed or dispersible, a stabilizing agent, a surfactant and an aqueous component. A commercial product known as "REVELATION" retexturizing complex for hands and chest sold by the same assignee contains a silicone gel material with an organopolysiloxane component and octamethylcyclotetrasiloxane.

Other examples of discussion of elastomer type materials and/or methods for processing such materials may be found in PCT cases WO 98/00097; WO 98/00104; WO 98/00105; WO 98/18438; WO 98/42307 all of which are incorporated herein by reference.

EP 0 787 758 A1 teaches a method for solvent thickening by using a silicone latex having a plurality of crosslinked polysiloxane particles.

PCT case WO 96/06594 assigned to Helene Curtis, Inc. describes a silicone-free surfactant or silicone-free surfactant blend having an HLB value of 0.1 to about 10, an organic phase comprising a volatile silicone compound or a volatile hydrocarbon compound, and water.

Borate cross-linkers useful in topically active compositions are described in EP 0 676 193 A2 to Helene Curtis, Inc.

These types of compositions are not totally satisfactory in cosmetic applications, especially underarm applications since they tend to synerese, form films, etc. Thus, there remains a need for improved formulations which exhibit improved properties and performance, especially in the area of aesthetics and efficacy.

In particular, one of the major problems with elastomer-containing formulations is the formation of a film after application to the surface of the skin. The hydrophobic nature of such a film may prevent an active ingredient (for example, an antiperspirant active) from reaching the targeted site (for example, when applied to the underarm area for antiperspirant/deodorant purposes).

Thus, it is an object of the present invention to provide cosmetic compositions which use selected silicone gel material to form compositions which leave little or no visible (white) residue on the skin, and which have improved properties especially in the areas of glidability, skin feel, smoothness, reduction in tack, reduced syneresis and increased efficacy.

It is another object of the invention to provide cosmetic compositions which reduce or eliminate the tendency to form films on the skin when applied in use, which might affect efficacy.

It is a further object of the invention to provide improved cosmetic compositions with the improvements as previously described and which are useful as antiperspirants and/or deodorants.

It is yet another object of this invention to provide cosmetic compositions which exhibit a reduction or elimination in the formation of films when applied to the skin surface.

It is still another object of the invention to provide underarm products containing an active ingredient which are made with a selected surfactant and which exhibit a reduction or elimination in the formation of films when applied to the skin surface with an increase in the efficacy of the antiperspirant active.

These and other objects of the invention will be apparent from the following description of the invention.

SUMMARY OF THE INVENTION

This invention comprises low residue cosmetic compositions (especially underarm products) which are made by combining an active ingredient; a silicone gel material itself comprising an elastomer composition; and at least one selected surfactant having an HLB value in the range of 8–16. The compositions of this invention exhibit reduced or eliminated film formation when applied to the skin and increased availability of the active ingredient.

DETAILED DESCRIPTION OF THE INVENTION

The cosmetic compositions of this invention can be made in the form of solids (for example, sticks (especially gel/sticks), gels, soft solids and creams) or liquids which have a viscosity of at least 1,000 centipoise ("cps").

The compositions of the present invention are made by combining:

(a) an active cosmetic material selected from the group consisting of antiperspirant active materials, deodorant active materials, insect repellents, antifungal agents, antibacterials agents, and fragrances;

(b) a silicone gel material which is made by combining:
(i) a cross-linked organopolysiloxane material as a gelling (solidifying) agent wherein the organopolysiloxane is made from a member selected from the group consisting of at least one silicone hydride cross-linking agent and at least one member selected from the group consisting of (A) a vinyl-terminated polysiloxane and (B) an alpha, omega diene; and
(ii) a liquid base vehicle for the gelling agent wherein the vehicle is made by combining at least one member of the group consisting of volatile silicone materials and non-volatile silicone materials, and optionally wherein at least one liquid emollient which is soluble or miscible in the selected silicone material(s) is added to form the vehicle (in this role the emollient is also referred to as "emollient material"); and (c) a nonionic surfactant having an HLB value of 8–16, particularly 8–12.

The cosmetically active ingredient is selected from the group consisting of antiperspirant active materials, deodorant active materials, insect repellents, antifungal agents, antibacterials agents, and fragrances. Formulations of particular interest are antiperspirants.

Where the composition contains an antiperspirant active, any of the known antiperspirant active materials can be utilized. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Antiperspirant actives can be incorporated into compositions according to the present invention in amounts in the range of 0.1–30%, preferably 15–25%, by weight, of the total weight of the composition. The amount used will depend on the formulation of the composition. For example, at amounts in the lower end of the broader range (for example, 0.1–10%), the antiperspirant active material will not substantially reduce the flow of perspiration, but will reduce malodor, for example, by acting as an antimicrobial material.

The antiperspirant active material is desirably included as particulate matter suspended in the composition of the present invention in amounts as described above, but can also be added as solutions or added directly to the mixture.

A deodorant fragrance may be used in an amount of 0.05–5.0% by weight based on the total weight of the composition.

An antimicrobial agent, for example bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban), silver halides, octoxyglycerin (Sensiva™ SC 50) and various zinc salts (for example, zinc ricinoleate) may also be included in formulations of the present invention. The bacteriostat can, illustratively, be included in the composition in an amount of 0.01–1.0% by weight, of the total weight of the composition. Triclosan, can illustratively be included in an amount of from 0.05% to about 0.5% by weight, of the total weight of the composition.

The silicone gel material includes at least one crosslinked organopolysiloxane material as a gelling agent and a vehicle as described herein. Each organopolysiloxane is made from a cross-linking agent and at least one member selected from the group consisting of siloxanes containing at least one vinyl group (hereinafter referred to as a "vinyl polysiloxane") and alpha omega dienes. Suitable vinyl polysiloxanes include:

(a) vinyl terminated polysiloxanes such as that of Formula I:

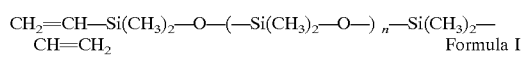

(b) vinyl functional copolymers such as that of Formula II:

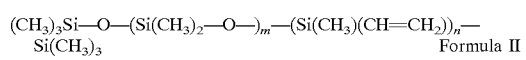

where n=a number from 1–100, particularly 10–50; and m=a number from 1–100, particularly 10–50.

Particular examples of vinyl polysiloxanes include, but are not limited to:

(a) polydimethylsiloxane, which is monovinyl terminated;
(b) vinylmethyl, dimethylsiloxane copolymer which is trimethylsiloxy terminated;
(c) vinylmethyl, dimethylsiloxane copolymer which is vinyl dimethyl terminated;
(d) divinylmethyl terminated polydimethyl siloxanes;
(e) vinyl Q-resin
(f) vinylphenylmethyl terminated dimethyl siloxanes;
(g) cyclic vinylmethyl dimethyl siloxanes;
(h) T-structure polydimethyl siloxanes with vinyl at branchpoint;
(i) T-structure polydimethyl siloxane with vinyl at branch terminus;
(j) diphenyl dimethyl copolymer which is vinyl terminated;
(k) vinyl terminated polydimethyl siloxanes;
(l) vinyl terminated trifluoropropyl methyl siloxane-dimethylsiloxane copolymer;
(m) vinyl terminated diethyl siloxane copolymer;
(n) vinyl methyl siloxane-dimethyl siloxane copolymer which is trimethylsiloxy terminated
(o) vinyl gums;
(p) vinyl methyl siloxane homopolymers; and
(q) mixtures of two or more of the foregoing.

Suitable alpha, omega dienes include those described in U.S. Pat. No. 5,880,210 (incorporated by reference in its entirety herein), especially those of Formula:

$CH_2=CH(CH_2)_xCH=CH_2$, where x is a number in the range of 1–20. Particular examples of suitable alpha, omega dienes include: 1,4-pentadiene; 1,5-hexadiene; 1,6-heptadiene; 1,7-octadiene; 1,8-nonadiene; 1,11-dodecadiene; 1,13-tetradecadiene; and 1,19-eicosadiene.

Suitable crosslinking agents include hydride terminated polydimethylsiloxanes of Formula III:

where p=a number from 1–50, particularly 5–20.

Particular examples of cross-linking agents are hydride functional polymers (≡SiH). Typical hybrid crosslinking agents are methylhydro-dimethylsiloxane copolymer with 20–60% methyl hydrogen. In selected circumstances hydride terminated siloxanes may be used for chain extension. Examples of suitable crosslinking agents include but are not limited to:

(a) methylhydrosiloxane-dimethylsiloxane copolymer;
(b) polymethylhydrosiloxanes;
(c) polyethylhydrosilane;
(d) polyphenyl-(dimethylhydrosiloxy)siloxane which is hydride terminated;
(e) methylhydrosiloxane-phenylmethylsiloxane copolymer which is hydride terminated; and
(f) methylhydrosiloxane-octylmethylsiloxane copolymer.

The reaction between a vinyl polysiloxane and a cross-linking agent may be accomplished in several ways:

(a) hydrosilylation addition reaction—This reaction relies on the ability of the hydrosilane bond (≡SiH) to add across a carbon-carbon double bond in the presence of noble metal catalysts, particularly platinum;

≡SiH+CH₂=CHSi≡→≡SiCH₂CH₂S≡

(b) peroxide induced free radical reactions—These reactions are an adaptation of conventional organic chemistry and relies on the availability of C—H bonds (already present in the methyl groups of the polydimethylsiloxane) to effect the cross-linking. These reactions use peroxide or radiation to initiate cross-linking. The peroxide-induced cross-linking can be achieved by using two categories of peroxide, the so-called vinyl specific catalysts, such as aryloxy peroxides, which do not need the vinyl groups to effect cross-linking. In the case of vinyl specific peroxides the level of vinyl functionality needed to achieve the desired level of cross-linking is typically in the range of 0. 1–0.15% weight/weight of the polymer. For polydimethylsiloxane and diaryloxyperoxides the cure mechanism proceeds by hydrogen abstraction from the ≡Si—CH₃, by the peroxy radical, followed by combination of the resulting ≡SiĊH₂ radicals formed to give a ≡SiCH₂CH₂Si≡ cross-link:

ArOOAr→2ArȮ

ArȮ+CH₃Si≡→ArOH+ĊH₂Si≡

≡SiĊH₂+ĊH₂Si≡→≡SiCH₂CH₂Si≡

(c) condensation reactions—these reactions rely on the ability of some organic groups (such as alkoxy or acyloxy) attached to silicon (≡SiOR) to react with water to produce silanol (≡SiOH groups) which can then further react with the starting materials or another silanol group to produce a siloxane cross-link:

≡SiOR+HOH→≡SiOH+ROH then ≡SiOR+≡SiOH→≡SiOSi≡+ROH or ≡SiOH+≡SiOH→≡SiOSi≡+HOH and (d) hydridosilane/silanol reactions—Hydridosilane groups can react in a similar way as was described for condensation reactions; the reaction can be represented as either a one-step or two-step process:

≡SiH+≡SiOH→≡SiOSi≡+H₂ or ≡SiH+H₂O→≡SiOH+H₂

≡SiOH+≡SiOH→≡SiOSi≡+H₂O

In one particular example, a silicone gel as described in U.S. Pat. No. 5,654,362 to Schultz, Jr. et al (incorporated by reference in its entirety herein) is made by reacting an ≡Si—H containing polysiloxane with an alpha, omega-diene. The reaction is conducted in the presence of a platinum catalyst and in the presence of a low molecular weight silicone oil. The reaction is continued until a gel is formed by cross-linking and addition of ≡Si—H across double bonds in the alpha, omega-diene (CH₂=CH(CH₂)ₓ CH=CH₂, where x=1–20). Examples herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Akron, Ohio) under trade names KSG-15 (cyclomethicone (and) dimethicone/vinyl dimethicone crosspolymer), KSG-16 (dimethicone (and) dimethicone/vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Corning Corporation (Midland, Mich.) under trade name Dow Corning 9506 Cosmetic Powder; and a mixture of cyclomethicone and stearyl-vinyl/hydromethylsiloxane copolymer available from Grant Industries, Inc. (Elmwood Park, N.J.) under the trade name Gransil SR-CYC.

As described above, a liquid base vehicle for the gelling agent is used wherein the vehicle is made by combining at least one member of the group consisting of volatile silicone materials and non-volatile silicone materials, and optionally wherein at least one liquid emollient which is soluble or miscible in the selected silicone material(s) is added to form the vehicle.

The silicone materials used in providing the silicone gel material for forming the composition of the present invention may be selected from the group consisting of conventional cyclic and linear volatile and non-volatile silicones which act as a swelling agent for the suitable elastomer. Illustratively, and not by way of limitation, the volatile silicones are one or more members selected from the group consisting of cyclic polydimethylsiloxanes such as those represented by Formula IV:

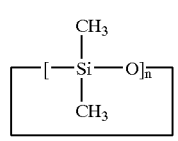

Formula IV where n is an integer with a value of 3–7, particularly 5–6. By volatile silicone material is meant a material that has a measurable vapor pressure at ambient temperature. For example, DC-345 fluid from Dow Corning Corporation (Midland, Michigan) is a type of cyclomethicone which can be used. These include a tetramer (or octylmethylcyclotetrasiloxane) and a pentamer (or decamethylcyclo-pentasiloxane). The nonvolatile and volatile linear silicones are one or more members selected from the group consisting of linear polydimethylsiloxanes such as those represented by Formula V:

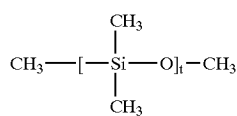

Formula V and t is selected so that the molecular weight ranges from 800–260,000 and the viscosity ranges from 5–600,000 centistokes, for example Dimethicone DC 200 from Dow Corning.

The vehicle may also be formed with at least one additional component selected from the group consisting of liquid emollients which are soluble or miscible in the silicone material(s) used to make the vehicle. By adding the additional liquid emollient to form the vehicle, such liquid emollient is characterized herein as part of the vehicle and not as part of the optional emollient additive which optional emollient additive may be added after the gel is formed. Liquid emollients suitable for use in forming a vehicle for this invention include any of those materials listed below under the full description of emollients provided they are liquids at room temperature and are soluble or miscible in the silicone materials selected to form the vehicle. Particular examples of such emollients useful in forming the vehicles for this invention include, but are not limited to:

(a) hydrocarbon—especially hydrogenated polyisobutene;

(b) esters—especially diisopropyl adipate, $C_{12-15}$ alkyl benzoates and neopentyl glycol diheptanoate; and (c) silicones and silanes—especially phenyl trimethicone and dimethicone.

Various techniques may be used to make gel materials from the elastomers listed above. These techniques include mechanical processes with high shear and/or high pressure for example, homogenization or sonolation (for example as described in PCT case WO 98/00104, and U.S. Pat. No. 5,854,336 both of which are incorporated by reference herein).

Silicone gel materials made from the elastomers described above are available from GE Silicones (Waterford, N.Y.) as GE 839; Grant Industries, Inc. (Elmwood Park, N.J.) as Gransil GCM; and Dow Corning Corporation (Midland, Mich.) as DC 9040. The elastomers used in this invention may be used in various concentrations, particle size distributions, viscosities and rheological profiles.

It is preferred that the silicone gel materials of the present invention have a select rheology profile. The rheology profile is defined herein in terms of the storage modulus (G'), the loss modulus (G") and the G"/G' ratio. The storage modulus represents how elastic or structured a sample is, the loss modulus represents how viscous a sample is. The numerical ratio G"/G' represents the extent to which the silicone gel materials exhibit certain viscous and elastic characteristics. Measurements for G' and G" for purposes of defining the silicone gel materials of the present invention may be determined at ambient conditions using conventional techniques known to those skilled in the art. For example, a CSL$^2$ 500 Controlled Stress Rheometer, available from TA Instruments, New Castle, Del., can be used with a plate configuration. A sample size of about 5 cubic centimeters of the silicone gel material to be evaluated is carefully sampled with minimal application of shear force and is placed between the plate fixtures on the rheometer for measurements of G' and G" in Pascals. The G"/G' ratio is then determined. The silicone gel materials should have a G"/G' ratio from about 0.001–50, preferably from 0.005–20, and more preferably, from 0.01–10. Compositions formulated with silicone gel materials with the above rheology profile exhibit improved product attributes and/or performance such as reduced syneresis, better spreadability, less balling, smoother application and better structure.

In the final cosmetic composition the silicone gel material can be included in the cosmetic composition in an amount of 10–80% by weight based on the total weight of the final cosmetic composition.

The surfactants useful in this invention have an HLB (hydrophilic-lipophilic balance) value of 8–16 (more particularly 8–12). The HLB parameter is a well known parameter the calculation of which is disclosed and explained in numerous references. This HLB value can be determined using the traditional HLB system, the Three Dimensional HLB system (which is tailored for silicones) or the Cohesive Energy Ratio theory based on solubility parameters as described in Griffin, W. C., *J. Soc. Cosmetic Chemists*, 1:311, (1949); O'Lenick, Jr., A. J., et al, *Cosmetics & Toiletries*, Vol. 3:37–44 (October 1996); Beenbower, A. et al, McCutcheon's Detergents and Emulsifiers, The Manufacturing Confectioner Publishing Co., Glen Rock, N.J. (1971) at pages 223–235; Fedors, R. F., *Polymer Engineering and Science*, Vol. 4, No.2 at pages 147–154 (February 1974). Any of these systems may be used to determine hydrophilicity and/or lipophilicity of a surfactant, although some variations may be obtained in HLB values. In particular, for nonionic surfactants, data obtained by actual analysis is usually a more accurate measure of HLB values (rather than theoretical determinations). For purposes of this invention it is intended that either the actual or theoretical HLB value may be used as the basis for selection.

With regard to nonionic surfactants, those used in this invention (which can also be a mixture or blend of surfactants) include, but are not limited to at least one member selected from the group consisting of:

(a) sorbitan esters and ethoxylated sorbitan esters (for example PEG-20 sorbitan isostearate, sorbitan monolaurate, polysorbate-20, polysorbate-40, polysorbate-60, polysorbate-80);

(b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10);

(c) ethoxylated adducts (for example, PEG-25 stearate, glyceryl stearate and PEG-100 stearate);

(d) PEG esters (for example, PEG-8 oleate, PEG-8 laurate, PEG-8 dilaurate, PEG-12 dilaurate, PEG-80 diisostearate, PEG-40 stearate);

(e) propoxylates (for example, PPG-10 butanediol, PPG-50 oleyl ether, PPG-2-ceteareth-9, PPG-3-deceth-3, PPG-5-ceteth-20);

(f) ethoxylated modified triglycerides (for example, PEG-20 corn glycerides, PEG-12 palm kernel glycerides);

(g) alkylphenol aromatic ethoxylates (for example, dinonylphenol ethoxylate with 9 moles of EO, octylphenol ethoxylate with 20 moles of EO, octylphenol ethoxylate with 40 moles of EO);

(h) block copolymers which are alkoxylated glycols having ethoxylated and propoxylated segments (for example, Poloxamers 182 and 234, Poloxamer 105 Benzoate, and Meroxapol 174);

(i) silicone polyethers (for example, (1) dimethicone copolyols (SILWET L-7087, L-7200 and L-7657; (2) dimethicone copolyol laurate (SILWAX WS-L); (3) dimethicone copolyol isostearate (SILWAX WS-IS); (4) polydimethicone copolyol (SILSOFT 477); (5) Eugenodimethicone copolyol (SILSOFT Shine); wherein the nonionic surfactant is selected so that it has an HLB (hydrophilic-lipophilic balance) value of 8–16 (more particularly 8–12).

The surfactant or blend of surfactants incorporated into the compositions of the present invention can, illustratively, be included in amounts of 0.1 –20%, preferably 0.5–10%, and more preferably 1–5%, by weight based on the total weight of the composition.

The compositions of the present invention can also include other optional ingredients to improve the aesthetics and/or performance of the cosmetic compositions of the invention. These include emollients, thickeners, colorants, fillers, fragrances, masking agents, etc.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

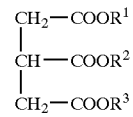

Formula VI wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO$—$OR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fuimarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length between 7 and 30, straight chain or branched. Specific examples include lauric, myristic, palmitic, stearic, oleic, linoleic and behenic acid.

(e) saturated and unsaturated fatty alcohols (including guerbet alcohols) with general structure $R^7COH$ where $R^7$ can be straight or branched and have carbon length of 7 to 30. Specific examples include lauryl, myristyl, cetyl, isocetyl, stearyl, isostearyl, oleyl, ricinoleyl and erucyl alcohol;
(f) lanolin and its derivatives which are a complex esterified mixture of high molecular weight esters of (hydroxylated) fatty acids with aliphatic and alicyclic alcohols and sterols. General structures would include $R^8CH_2$—$(OCH_2CH_2)_nOH$ where $R^8$ represents the fatty groups derived from lanolin and n=5 to 75 or $R^9CO$—$(OCH_2CH_2)_nOH$ where $R^9CO$— represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.
(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15. Specific examples include PPG-14 butyl ether and PPG-53 butyl ether.
(h) silicones and silanes the linear organo-substituted polysiloxanes which are polymers of silicon/oxygen with general structure:
  (i) $(R^{10})_3SiO(Si (R^{11})_2O)_xSi(R^{12})_3$
where $R^{10}$, $R^{11}$ and $R^{12}$ can be the same or different and are each independently selected from the group consisting of phenyl and C1–C60 alkyl;
  (ii) $HO(R^{14})_2SiO(Si (R^{15})_2O)_xSi(R^{16})_2OH$,
where R14, $R^{15}$ and $R^{16}$ the same or different and are each independently selected from the group consisting of phenyl and C1–C60 alkyl; or
   (iii) organo substituted silicon compounds of formula $R^{17}Si(R^{18})OSiR^{19}$ which are not polymeric where $R^{17}$, $R^{18}$ and $R^{19}$ can be the same or different and are each independently selected from the group consisting of phenyl and C1-C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.
  (i) mixtures and blends of two or more of the foregoing.

The emollient or emollient mixture or blend thereof incorporated in compositions according to the present invention can, illustratively, be included in amounts of 0.5–50 %, preferably 1–25 %, more preferably 3–12 %, by weight, of the total weight of the composition.

Another category of optional ingredients useful in this invention is thickeners which may be added to increase the viscosity, improve aesthetics and/or improve the performance of the cosmetic compositions of the invention. Suitable thickeners include one or more members selected from the group consisting of:
(a) high melting point waxes (65–101 degrees C.) such as beeswax, montan, ozokerite, ceresin, paraffin, hydrogenated castor oil, and C26–C50 linear alcohols;
(b) low melting point waxes (37–65 degrees C.) such as fatty alcohols, fatty acids, fatty acid esters, fatty acid amides and particularly stearyl alcohol, cetyl alcohol, stearic acid and polydimethyl siloxanyl beeswax;
(c) silicone waxes such as methyl alkyl silicone waxes and ester silicone waxes, particularly stearoxytrimethylsilane, stearyldimethicone, dimethiconol behenate and C30–45 alkyl methicone;
(d) modified natural polymers such as those which are cellulose or guar based, particularly cellulose gum, hydroxyethylcellulose, methylcellulose, hydroxypropylmethylcellulose, hydroxypropyl guar;
(e) synthetic polymers such as alkylene/alkylene oxide polymers, particularly polyethylene, oxidized polyethylene, ethylene/acrylate copolymer, ethylene/vinyl acetate copolymer, PEG-n (where n is a number from 4–90,000) and PEG-m stearate (where m is a number from 2–175);
(f) inorganic smectite clays such as smectite clays and amorphous silicon dioxide particularly hectorite, sodium magnesium silicate, stearalkonium hectorite, Quaternium-18 hectorite, bentonite, magnesium aluminum silicate, Quatemium-18 bentonite, stearalkonium bentonite, hydrated silica, and silica;
(g) trihydroxystearin and tribehenin;
(h) mixtures and blends of any of the foregoing.

For thickeners of groups a, b, and c, the addition levels are in the range of 0.05–25 percent by weight (preferably 2–17 percent) based on the total weight of the composition. For thickeners of groups d, e, f and g, the addition levels are in the range of 0.01–10% by weight (preferably 0.1–5 percent) based on the weight of the total composition.

The amounts of surfactants, emollients and thickeners can be selected on the basis of the form desired and in combination with the amount of silicone gelling agent used.

Other various optional components include those described in U.S. Pat. No. 5,019,375 to Tanner et al; U.S. Pat. No. 4,937,069 to Shin; and U.S. Pat. No. 5,102,656, each of which is incorporated by reference in its entirety herein. Examples of such additional ingredients include fragrances, insect repellents, coloring agents, opacificers, etc. in types and amounts conventionally used for such products.

The compositions of the invention may take various forms depending on the amount of silicone gel material and the amount of other ingredients used; some of the more preferable compositions are soft solids or gels. For example, a silicone gel may be made which comprises 1–30% by weight (based on the total weight of the silicone gel material) of at least one cross-linked organopolysiloxane material; and 70–99% by weight (based on the total weight of the silicone gel material) of the vehicle used (for example, cyclomethicone).

Compositions according to the present invention can be made by mixing the silicone gel material with surfactant(s), active ingredient(s) and optionally one or more of emollient (s), thickener(s) and fragrance. Mixing conditions and the use of heating will depend on what types of materials are being combined and; the melting points for those materials as are known to those skilled in the art. For example if soft solids, roll-ons or gels are being made, temperatures, in the range of room temperature or slightly higher (for example, 25–50 degrees C., particularly 23–30 degrees C.) may be used. For stick products and soft solid/cream products made with higher melting point materials (for example, high temperature waxes) temperatures from 25–85 degrees C. may be used. The mixture can be introduced into dispensing containers known to those skilled in the art including those for solids, gels, roll-ons, soft solids and creams. In one particular example, slotted dispensers may be used such as those known in the art, for example, those having a parallel row or rows of straight or curved slots or holes with a screw mechanism for forcing the composition through the top as the product is used.

Where the dispensing containers have a top surface with slots therein, the composition can be rubbed onto the skin from the top surface of the container (itself fed from a reservoir of product in the container) so as to deposit an adequate amount of the cosmetic composition on to the skin. The cosmetic composition, for example, an antiperspirant and/or deodorant in the form of a soft solid, can be extruded from inside the dispensing container through the slots or holes onto the top of the surface of the dispensing container, and from there may be applied to the skin in the axillary regions to deposit sufficient amounts of antiperspirant and/or deodorant active material to reduce body malodor and/or reduce perspiration in axillary regions of the human body.

Various forms of the invention can be exemplified by the following formulations but should not be construed as limitations on the invention:

Antiperspirant Stick 1) 0.5–10% (preferably 2–8%) silicone gelling agent, for example, cyclopentasiloxane cetearyl dimethicone/vinyl crosspolymer.
2) 30–70% (preferably 40–50%) vehicle for the gelling agent, for example, volatile cyclic silicones.
3) 8–25% (preferably 20–22%) antiperspirant active, for example, a ZAG complex.
4) 0.5–10% (preferably 1–5%) surfactant selected from the group of nonionics (for example, Dimethicone copolyol, PEG 30 Castor oil, PEG 8 Dilaurate, PPG-1-PEG-9 Lauryl Glycol Ether, Dimethicone copolyol EO/PO polyether, Dimethicone copolyol laurate and mixtures thereof).
5) 1–15% (preferably 3–10%) emollients selected from the group consisting of hydrocarbons (for example, hydrogenated polyisobutene), fatty acid esters (for example, $C_{12-15}$ alkyl benzoate, diisopropyl adipate and neopentyl glycol diheptanoate), or silicone materials (for example, dimethicone), wherein a portion or all of the emollients may be combined to make the vehicle and any remainder portion of emollients may be added for an emollient effect.
6) thickeners such as one or more members selected from the group consisting of (a) 10–25% (preferably 14–22%) (for example, stearyl alcohol, isostearyl alcohol, cetyl alcohol, silicone waxes, hydrogenated castor oil and mixtures thereof) and (b) 0. 1–5% (preferably 0.2–2.0%) of at least one of the members of the group consisting of silica, cellulose, polyethylene and mixtures thereof.
7) 0.05–5.0% (preferably 0.7–1.2%) fragrance.

Antiperspirant Gel/Soft solid/Cream 1) 0.5–10% (preferably 2–6%) silicone gelling agent, for example, cyclopentasiloxane cetearyl dimethicone/vinyl crosspolymer.
2) 40–80% (preferably 50–70%) vehicle for gelling agent, for example, volatile cyclic silicones.
3) 8–25% (preferably 20–22%) antiperspirant active, for example, a ZAG complex.
4) 1–8% (preferably 2–6%) surfactant selected from the group of nonionics, for example, Dimethicone copolyol, PEG 30 Castor oil, PEG 8 Dilaurate, PPG-1-PEG-9 Lauryl Glycol Ether, Dimethicone copolyol EO/PO polyether, Dimethicone copolyol laurate and mixtures thereof).
5) 1–15% (preferably 3–10%) emollients selected from the group consisting of hydrocarbons (for example, hydrogenated polyisobutene), fatty acid esters (for example, $C_{12-15}$ alkyl benzoate, diisopropyl adipate and neopentyl glycol diheptanoate), or silicone materials (for example, dimethicone), wherein a portion or all of the emollients may be combined to make the vehicle and any remainder portion of emollients may be added for an emollient effect.
6) thickeners such as one or more members selected from the group consisting of (a) 1–15% (preferably 2–8%) (for example, stearyl alcohol, isostearyl alcohol, cetyl alcohol, silicone waxes, hydrogenated castor oil and mixtures thereof) and (b) 0. 1–5% (preferably 0.2–2.0%) of at least one of the members of the group consisting of silica, cellulose, polyethylene and mixtures thereof.
7) 0.05–5.0% (preferably 0.7–1.2%) fragrance.

Antiperspirant Roll On 1) 0.1–10% (preferably 0.5–3%) silicone gelling agent, for example, cyclopentasiloxane cetearyl dimethicone/vinyl crosspolymer.
2) 50–80% (preferably 60–70%) vehicle for gelling agent, for example, volatile cyclic silicones.
3) 8–25% (preferably 20–22%) antiperspirant active, for example, a ZAG complex.
4) 1–8% (preferably 2–6%) surfactant selected from the group of nonionics, for example, Dimethicone copolyol, PEG 30 Castor oil, PEG 8 Dilaurate, PPG-1-PEG-9 Lauryl Glycol Ether, Dimethicone copolyol EO/PO polyether, Dimethicone copolyol laurate and mixtures thereof).
5) 1–15% (preferably 3–10%) emollients selected from the group consisting of hydrocarbons (for example, hydrogenated polyisobutene), fatty acid esters (for example, $C_{12-15}$ alkyl benzoate, diisopropyl adipate and neopentyl glycol diheptanoate), or silicone materials (for example, dimethicone), wherein a portion or all of the emollients may be combined to make the vehicle and any remainder portion of emollients may be added for an emollient effect.
6) thickeners such as one or more members selected from the group consisting of (a) 1–15% (preferably 2–8%) (for example, stearyl alcohol, isostearyl alcohol, cetyl alcohol, silicone waxes, hydrogenated castor oil and mixtures thereof) and (b) 0. 1–5% (preferably 0.2–2.0%) of at least one of the members of the group consisting of silica, cellulose, polyethylene and mixtures thereof.
7) 0.05–5.0% (preferably 0.7–1.2%) fragrance.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., $7^{th}$ ed. 1997). Mixing techniques used to make the compositions are those conventionally used in the art including those described above.

Examples 1–81

Preliminary Evaluation

Mixture 1 is made by combining 5.0% Cyclopentasiloxane Cetearyl Dimethicone/Vinyl Crosspolymer, 73.5%

Cyclomethicone (70% pentamer+30% hexamer), and 22.5% aluminum zirconium tetrachlorhydrex glycine complex (all amounts based on weight percents). A 2 gram samples of a test example is prepared by mixing 95% weight percent of Mixture 1 with 5% of a selected surfactant from the surfactants listed in Table 1 to make a series of Mixture 2's. A sample (0.1 gram) of each test example as Mixture 2 is blotted (2 cm diameter circular area) onto a swatch of black cloth (100% cotton fabric, 7.5 cm×10 cm) which has been placed and taped on a black ceramic tile). The initial time is recorded. A Control sample is prepared without the surfactant and also applied to a fabric swatch in the same manner. Blot positions are marked for each one. The blots are allowed to dry for 20 minutes. Deionized water (1 drop) is applied to the top of each dried blot. The time needed for each water drop to be absorbed through the cloth is recorded (Absorption Time). This is apparent when the top surface of the drop is observed to be level with the flat surface of the cloth. The examples with absorption times less than 10 minutes and preferably less than 5 minutes were deemed to predict effectiveness in solubilizing film in the context of this invention. Correspondingly, those examples with absorption times >45 minutes were deemed not to favor favorable solubilizing properties. The data obtained for evaluations of various surfactants as well as HLB values obtained through literature references are shown in Table 1 or experimentally determined using water solubility.

TABLE 1

| | | Absorption Time (minutes) | HLB |
|---|---|---|---|
| CONTROL (sample without surfactant) | | >45 | N/A |
| Sorbitan & Ethoxylated Sorbitan Esters | | | |
| Ex. 1. | Sorbitan Monolaurate (SPAN 20, ICI) | 22 | 8.6 |
| Ex. 2. | Sorbitan Monopalmitate (SPAN 40, ICI) | 20 | 6.7 |
| Ex. 3. | Sorbitan Monostearate (SPAN 60, ICI & Arlacel 60, ICI) | >45 | 2.1 |
| Ex. 4. | Sorbitan Isostearate (CRILL 6, Croda) | 30 | 4.6 |
| Ex. 5. | Sorbitan Monooleate (SPAN 80, ICI) | >45 | 4.3 |
| Ex. 6. | Polysorbate 20 (TWEEN 20, ICI) | 5 | 16.7 |
| Ex. 7. | Polysorbate 40 (TWEEN 40, ICI) | 1 | 15.6 |
| Ex. 8. | Polysorbate 60 (TWEEN 60, ICI) | 1 | 14.9 |
| Ex. 9. | Polysorbate 80 (TWEEN 80, ICI) | 5 | 15.0 |
| Ex. 10. | Polysorbate 120 (CRILLET 6, Croda) | 3 | 14.9 |
| Ex. 11. | PEG-20 Sorbitan Beeswax (G-1726, ICI) | 3 | |
| Ethoxylates | | | |
| Ex. 12. | Ceteth 20 (Cetomacrogol 1000 BP, Croda) | 3 | 15.6 |
| Ex. 13. | PEG 30 Castor Oil (INCROCAS 30, Croda) | 3 | 13.0 |
| Ex. 14. | PEG 40 Hydrogenated Castor oil (CREMAPHOR RH-40, BASF) | 3 | 14–16 |
| Ex. 15. | PEG 60 Hydrogenated Castor oil (CREMAPHOR RH-60, BASF) | 3 | 14–16 |
| Ex. 16. | Ceteareth 12 (EMULGEN B-1, Henkel) | 3 | |
| Ex. 17. | Ceteareth 20 (INCROPOL CS-20, Croda) | 1 | 15.5 |
| Ex. 18. | Ceteareth 20 (EMULGEN B-2, Henkel) | 1 | 15.5 |
| Ex. 19. | PPG 5 Ceteth 20 (PROCETYL AWS, Croda) | 4 | 16.0 |
| Ex. 20. | PPG 3 Buteth 5 (UCON50-HB-100 Union Carbide) | 3 | 13+ |
| Ex. 21. | Steareth 2 (VOLPO S-2, Croda) | 5 | 4.9 |
| Ex. 22. | Steareth 2 (BRIJ 72, ICI) | 5 | 4–6 |
| Ex. 23. | Steareth-10 (VOLPO S-10, Croda) | 3 | 12.4 |
| Ex. 24. | Steareth-20 (VOLPO S-20, Croda) | 1 | 15.5 |
| Ex. 25. | Steareth-21 (BRIJ 721S, ICI) | 8 | 14–16 |
| Ex. 26. | Steareth-100 (BRIJ 700, ICI) | 15 | 18.8 |
| Ex. 27. | Oleth-5 (VOLPO 5, Croda) | 0.5 | 8.8 |

TABLE 1-continued

| | | Absorption Time (minutes) | HLB |
|---|---|---|---|
| Ex. 28. | Oleth-9 (Phenoxolol-9, Phoenix Chemical Company) | 0.5 | 10–13 |
| Ex. 29. | Oleth-10 (VOLPO 10, Croda) | 1 | 12.4 |
| Ex. 30. | Oleth-20 (RHODASURF ON-870, Rhone Poulenc) | 8 | 15.4 |
| Ex. 31. | Oleth-20 (RHODASURF ON-877, Rhone Poulenc) | 3 | 15.4 |
| Ethoxylated Adducts | | | |
| Ex. 32. | PEG 25 PG Stearate (G-2162, ICI) | 4 | 11.0 |
| Ex. 33. | Glyceryl Stearate and PEG 100 Stearate (ARLACEL 165, ICI) | 30 | 11.0 |
| Alcohol Esters | | | |
| Ex. 34. | Myristyl Myristate (ALKAMULS MM/M, Rhone Poulenc) | >45 | |
| Glycol Esters | | | |
| Ex. 35. | Glyceryl Monostearate (CUTINA GMS, Henkel) | >45 | |
| PEG Esters | | | |
| Ex. 36. | PEG 8 Oleate (ALKAMULS 400-MO, Rhone Poulenc) | 1 | 11.0 |
| Ex. 37. | PEG 12 Dilaurate (JEEMATE 600-DL, Jeen) | 1 | |
| Ex. 38. | PEG 8 Dilaurate (JEEMATE 400-DL, Jeen) | 1 | 10–13 |
| Ex. 39. | PEG 8 Laurate (JEEMATE 400-ML, Jeen) | 1 | 13+ |
| Ex. 40. | PEG 8 Distearate (PEG-400 Distearate, Stepan) | 6 | 10–13 |
| Ex. 41. | PEG 40 Stearate (MYRJ 52, ICI) | 5 | 15–17 |
| Ex. 42. | PEG 80 Diisostearate (PEG 4000 Diisostearate, Scher) | 35 | |
| Propoxylates | | | |
| Ex. 43. | PPG 10 Butanediol (Probutyl DB-10, Croda) | 5 | 10–13 |
| Ex. 44. | PPG 10 Cetyl ether (Procetyl 50, Croda) | >45 | 1–4 |
| Ex. 45. | PPG 11 Stearyl ether (WITCONOL APS, Witco) | 10 | 1–4 |
| Ex. 46. | PPG 3 Myristyl ether (Promyristyl PM-3) | 10 | 1–4 |
| Ex. 47. | PPG 50 Oleyl ether (PROVOL 50, Croda) | 30 | 1–4 |
| Ex. 48. | PPG-1-PEG-9 Lauryl Glycol Ether (EUMULGIN L, Henkel) | 1 | 13+ |
| Ex. 49. | PPG 2 Myristyl ether propionate (CRODAMOL PMP, Croda) | >45 | 1–4 |
| Alkylphenol Aromatic Ethoxylates | | | |
| Ex. 50. | Octylphenol Ethoxylate (IGEPAL CA-877, Rhone Poulenc) | 45 | 17.4 |
| Ex. 51. | Octylphenol Ethoxylate (IGEPAL CA897, Rhone Poulenc) | >45 | 18.0 |
| Ex. 52. | Dinonylphenol Ethoxylate (IGEPAL DM-530, Rhone Poulenc) | 1 | 9.4 |
| Block Copolymers | | | |
| Ex. 53. | Poloxamer 182 (ANTAROX L-62, Rhone Poulenc) | 6 | 7.0 |
| Ex. 54. | Poloxamer 234 (ANTAROX P-84, Rhone Poulenc) | 3 | 14.0 |
| Ex. 55. | Meroxipol 174 (ANTAROX 17-R-4, Rhone Poulenc) | >45 | 4–7 |
| Silicone Polyethers | | | |
| Ex. 56. | Polydimethicone Copolyol (SILSOFT 477, Witco Organosilicones) | 7 | 1–4 |
| Ex. 57. | Dimethicone Copolyol, (SILWET L-7622, Witco Organosilicones) | 25 | 5–8 |
| Ex. 58. | Dimethicone Copolyol, (SILWET L-7087, Witco Organosilicones) | 1 | 9–12 |
| Ex. 59. | Dimethicone Copolyol, (SILWET L-7200, Witco Organosilicones) | 2 | 13–17 |

TABLE 1-continued

| | | Absorption Time (minutes) | HLB |
|---|---|---|---|
| Ex. 60. | Dimethicone Copolyol, (SILWET L-7657, Witco Organosilicones) | 1 | 13–17 |
| Ex. 61. | Eugeno Dimethicone Copolyol (SILSOFT Shine, Witco Organosilicones) | 1 | 10–13 |
| Ex. 62. | Polyglyceryl-4 Isostearate & Cetyl Dimethicone Copolyol & Hexyl Laurate (ABIL WE 09, Goldschmidt) | 15 | 1–4 |
| Ex. 63. | Dimethiconol Stearate (SILWAX S, Lambent Technologies) | >45 | |
| Ex. 64. | Dimethiconol Castorate (SILWAX C, Lambent Technologies) | >45 | |
| Ex. 65. | Dimethicone Copolyol Isostearate (SILWAX WD-IS, Lambent Technologies) | 1 | |
| Ex. 66. | Dimethicone Copolyol Laurate (SILWAX WS-L, Lambent Technologies) | 1 | 9.4 |
| Ex. 67 | Dimethicone Copolyol (ABIL B 8830, Goldschmidt) | 7 | 3–6 |
| Ex. 68 | Dimethicone Copolyol (ABIL B 8852, Goldschmidt) | 1 | 6–8 |
| Ex. 69 | Dimethicone Copolyol (ABIL B 8863, Goldschmidt) | 7 | 13+ |
| Ex. 70 | Dimethicone Copolyol (SILWET L-7001, Witco) | 2 | 9–12 |
| Ex. 71 | Dimethicone Copolyol (SILWET L-7002, Witco) | 2 | 9–12 |
| Ex. 72 | Dimethicone Copolyol (SILWET L-7230, Witco) | 3 | 9–12 |
| Ex. 73 | Dimethicone Copolyol (SILWET L-7280, Witco) | 10 sec | 8 |
| Ex. 74 | Dimethicone Copolyol (SILWET L-7500, Witco) | 10 | 5 |
| Ex. 75 | Dimethicone Copolyol (SILWET L-7600, Witco) | 1.5 | 13–17 |
| Ex. 76 | Dimethicone Copolyol (SILWET L-7602, Witco) | 5 sec | 8 |
| Ex. 77 | Dimethicone Copolyol (SILWET L-7604, Witco) | 1 | 13–17 |
| Ex. 78 | Dimethicone Copolyol (SILWET L-7607, Witco) | 1 | 13–17 |
| Ex. 79 | Dimethicone Copolyol (SILWET L-7608, Witco) | 10 sec | 8 |
| Ex. 80. | Dimethicone Copolyol (DOW 190, Dow Corning) | 20 sec | 10–13 |
| Ex. 81 | Dimethicone Copolyol (DOW 193, Dow Corning) | 20 sec | 13+ |

Examples 82–97

Second Level Evaluation: Nature of the Film

After the evaluation described in Examples 1–81 was completed, a second level test was used to demonstrate the effectiveness of selected surfactants to form a solubilizable film by evaluating the nature of the film in selected compositions. A 1 kilogram batch was prepared for selected sample formulations using the amounts of materials listed in Tables 2–5 below. Silicone gel material was added to a beaker. The surfactants (such as PEG-8 distearate, dimethicone copolyol) were added. Next the active cosmetic material was added. The ingredients were added in the order listed above and mixed with homogenization. A portion of each sample (as described in the compositions in Tables 2–5) (1 gram) is applied evenly on the bottom of a petri dish. The coated dish is placed in an oven (37° C.) for one hour. The dish is removed from the oven and distilled water (10 gm) is then added to the dish. The sample is shaken gently for two hours. Water is decanted from the dish and the dish is then allowed to air dry. Hydrophobicity/hydrophilicity on dried sample was obtained by placing a drop of water and visually examining for droplet shape (also characterized in having a contact angle greater or less than 90 degrees). This position may be evaluated by measuring the contact angle beTWEEN a liquid (water), a substrate (film on petri dish, fiber surface, etc.) and air. For hydrophobic films, the contact angle is greater than 90 degrees because the water does not wet the film and thus beads up. For hydrophilic films, the contact angle is less than 90 degrees because the water wets the film and increases contact. The data for this evaluation is found in Tables 2–5; those samples noted as being hydrophilic are preferred.

Examples 82–97

Third Level Evaluation: Release of Active

The types of samples described above under Examples 82–97—Second Level Evaluation were also subjected to a further test. Since release of the active from the matrix of an antiperspirant is necessary for clinical efficacy of antiperspirant products, an evaluation of the quantity of aluminum and zirconium released from the antiperspirant matrix in in vitro conditions may be performed. For sample preparation cotton pads (10 cm×10 cm), made of Webril® cotton pads (Kleantest) are cut and an application zone, in the form of the disk (7 cm diameter) is marked in the center of the cotton pad. A thin layer of silicone elastomer composition (0.9 gram) is applied to the application zone. The silicone elastomer composition is dried to about 10% of its original weight. A sample (0.75 grams) of antiperspirant product is applied on a Webril® pad and the pad is folded into a 3.3 cm square. The sample holder is then placed into a dissolution vessel of the dissolution apparatus. A U.S.P. dissolution apparatus (VK7000, Vankel Industries, Cary, N.C.) is used to study the dissolution of the aluminum/zirconium complexes from the antiperspirant product. The dissolution medium (200 ml of deionized, degassed water) is placed in 200 ml dissolution vessels. Stirring of the medium is done with 200 rpm rotation of stainless steel paddles (type 316 ¼" (0.64 cm) diameter shaft). The vessels are submerged in a temperature controlled (37.5° C.) water bath. Sampling of the medium (5 ml) is obtained by a dissolution sampling station (VK 8000, Vankel Industries). The sample aspiration is provided by a bi-directional peristaltic pump. Following sampling, the sampled volume is replaced with fresh medium. Sampling periods are each set at 120 minutes. Samples are collected in disposable culture tubes (Kimax® 51, borosilicate glass 16×100), and 5 ml of a 10% (weight/weight) nitric acid solution in water are added to provide complete solubility of the Al and Zr species. The samples are then analyzed by Inductively Coupled Plasma (ICP), and the concentration of aluminum and zirconium is calculated down to a sensitivity of 0–100 ppm. Standards of aluminum and zirconium at concentrations of 50 ppm and 100 ppm may be included in the calibration of the equipment. The results are expressed as a function of the % Al or % Zr released based on the total amount of aluminum and zirconium contained in the products. The concentration measured by ICP is converted into a measurement of total aluminum amount released measured by ICP:

$$Q_{ICP}=C_{ICP} \times 200 \times 2$$

where $Q_{ICP}$=the quantity of aluminum detected by ICP and $C_{ICP}$=the concentration of aluminum detected by ICP. The % released is a function of the amount of aluminum released and the total aluminum present in the sample as per the formula:

$$\% \text{ Release}=100 \times Q_{ICP}/Q_0$$

where $Q_0$ is the original amount of the aluminum in the sample (in grams). $Q_0$ can be calculated using the following formula:

$$Q_0 = \%\text{aluminum in salt (COA)} \times (\%\text{salt in formula}) \times (\text{sample}/10000)$$

COA=the value from the certificate of analysis of the antiperspirant active. Measurements were taken 120 minutes after application. The data is found in Tables 2–5 under Release %. The samples showing the higher amounts of release compared to the control are preferred.

TABLE 2

| Ingredients | Control #1 | Ex. 82 | Ex. 83 | Ex. 84 | Ex. 85 |
|---|---|---|---|---|---|
| Cyclomethicone/Elastomer Blend | 65.05 | 65.05 | 65.05 | 65.05 | 65.05 |
| Aluminum-Zirconium Tetrachlorohydrex gly | 22.5 | 22.5 | 22.5 | 22.5 | 22.5 |
| Ex. 80 Surfactant | | 2 | | | |
| Ex. 81 Surfactant | | | 2 | | |
| Ex. 66 Surfactant | | | | 2 | |
| Ex. 59 Surfactant | | | | | 2 |
| q.s. Cyclomethicone (SF 1202) | 12.45 | 10.45 | 10.45 | 10.45 | 10.45 |
| Release % | 72 | 71 | 69 | 83 | 79 |
| Nature of the Film | Hydrophobic | Hydrophilic | Hydrophilic | Hydrophilic | Hydrophilic |

TABLE 3

| Ingredients | Control #1 | Ex. 86 | Ex. 87 | Ex. 88 | Ex. 89 |
|---|---|---|---|---|---|
| Cyclomethicone/Elastomer Blend | 65.05 | 65.05 | 65.05 | 65.05 | 65.05 |
| Aluminum-Zirconium Tetrachlorohydrex gly | 22.5 | 22.5 | 22.5 | 22.5 | 22.5 |
| Ex. 48 Surfactant | | 2 | | | |
| Ex. 61 Surfactant | | | 2 | | |
| Ex. 19 Surfactant | | | | 2 | |
| Ex. 13 Surfactant | | | | | 2 |
| q.s. Cyclomethicone (SF 1202) | 12.45 | 10.45 | 10.45 | 10.45 | 10.45 |
| Release % | 72 | 81 | 67 | 67 | 74 |
| Nature of the Film | Hydrophobic | Hydrophilic | Hydrophilic | Hydrophilic | Hydrophilic |

TABLE 4

| Ingredients | Control #1 | Ex. 90 | Ex. 91 | Ex. 92 | Ex. 93 |
|---|---|---|---|---|---|
| Cyclomethicone/Elastomer Blend | 65.05 | 65.05 | 65.05 | 65.05 | 65.05 |
| Aluminum-Zirconium Tetrachlorohydrex gly | 22.5 | 22.5 | 22.5 | 22.5 | 22.5 |
| Ex. 32 Surfactant | | 2 | | | |
| Ex. 37 Surfactant | | | 2 | | |
| Ex. 31 Surfactant | | | | 2 | |
| Ex. 36 Surfactant | | | | | 2 |
| q.s. Cyclomethicone (SF 1202) | 12.45 | 10.45 | 10.45 | 10.45 | 10.45 |
| Release % | 72 | 66 | 63 | 56 | 66 |
| Nature of the Film | Hydrophobic | Hydrophilic | Hydrophilic | Hydrophobic | Hydrophilic |

TABLE 5

| Ingredients | Control #1 | Ex. 94 | Ex. 95 | Ex. 96 | Ex. 97 |
|---|---|---|---|---|---|
| Cyclomethicone/Elastomer Blend | 65.05 | 65.05 | 65.05 | 65.05 | 65.05 |
| Aluminum-Zirconium Tetrachlorohydrex gly | 22.5 | 22.5 | 22.5 | 22.5 | 22.5 |
| Ex. 24 Surfactant | | 2 | | | |
| Ex. 6 Surfactant | | | 2 | | |
| Ex. 7 Surfactant | | | | 2 | |
| Ex. 60 Surfactant | | | | | 2 |
| q.s. Cyclomethicone (SF 1202) | 12.45 | 10.45 | 10.45 | 10.45 | 10.45 |
| Release % | 72 | 54 | 59 | 59 | 66 |
| Nature of the Film | Hydrophobic | Hydrophobic | Hydrophilic | Hydrophilic | Hydrophilic |

Examples AA–DD

Antiperspirant/Deodorant Cream: Comparison of Invention

Compositions may be made using the ingredients listed in Table 6.

TABLE 6

| Ingredient | Example AA | Example BB | Example CC | Example DD |
|---|---|---|---|---|
| Cyclopentasiloxane (and) Cetearyl Dimethicone/ Vinyl Dimethicone Crosspolymer | 64.25 | 65.05% | 65.25 | 63.05 |
| Aluminum zirconium tetrachlorohydrex gly | 22.50 | 22.50 | 25.00 | 25.00 |
| Neopentyl glycol diheptanoate | 0.00 | 5.00 | 0.00 | 0.00 |
| C12–15 alkyl benzoate | 3.00 | 3.00 | 8.25 | 0.00 |
| PEG-8 distearate | — | 2.00 | — | — |
| Diisopropyl adipate | 5.00 | 0.00 | 0.00 | 0.00 |
| Phenyl trimethicone | 0.00 | 0.00 | 0.00 | 8.25 |
| Dimethicone copolyol laurate | 2.00 | 0.00 | 0.00 | 2.00 |
| Dimethicone copoylol | 0.00 | 1.00 | 1.00 | 1.00 |
| Stearyl dimethicone | 0.75 | 0.75 | 0.00 | 0.00 |
| Silica | 0.00 | 0.20 | 0.00 | 0.20 |
| Fragrance | 0.50 | 0.50 | 0.50 | 0.50 |
| Total | 100.00 | 100.00 | 100.00 | 100.00 |

For evaluating aesthetic properties, a composition made with the composition of Example BB was compared on the basis of aesthetics with Example 4 from PCT case WO 97/44010. Sample BB was a soft solid having the composition described in Table 6. A 1 kilogram batch was prepared for selected sample formulations using the amounts of materials listed in Table 6. Silicone gel material was added to a beaker. The surfactants (such as PEG-8 distearate, dimethicone copolyol) and emollients (such as C12–15 alkyl benzoate and neopentyl glycol diheptanoate) were added. Next the active cosmetic material was added. Next the thickeners (for example, silica or stearyl dimethicone) were added. Finally the fragrance was added. The ingredients were added in the order listed above and mixed with homogenization. Sample XX was made with 70% Gransil GCM, 20% Al—Zr tetrachlorohydrex gly and 10% Dimethicone. A group of 20 in-house panelists was used. For each individual, a portion of each of Sample BB and Sample XX (about 0.2 grams of each) was applied at the back of each arm. The area of the forearm is marked. Both samples were applied by the panelists scooping each sample from a dish with the forefinger and rubbing the sample with upward/downward strokes ten times on the marked area. Evaluations were made and the results are shown in Table 7. The numbers indicate the number of panelists responding in the indicated category. The data shows the superiority of a composition of the invention.

TABLE 7

| Attribute | Sample BB | Sample XX |
|---|---|---|
| Less Wet | 7 | 12 |
| Less Oily | 6 | 14 |
| More Drag - During Application | 5 | 14 |
| More Drag- Immediately After Application | 5 | 14 |
| More Drag - After 5 Minutes | 3 | 16 |

TABLE 7-continued

| Attribute | Sample BB | Sample XX |
|---|---|---|
| More Tack | 7 | 13 |
| Less Whitening | 16 | 4 |

Examples EE–GG

The conventional mixing methods described above were used to make products with the ingredients shown in Table 8.

TABLE 8

| Ingredient | Example EE | Example FF | Example GG |
|---|---|---|---|
| Cyclopentasiloxane (and) Cetearyl Dimethicone/Vinyl Dimethicone Crosspolymer | 63.05 | 62.50 | — |
| Cyclopentasiloxane (and) Cetearyl Dimethicone Crosspolymer | — | — | 60.8 |
| Aluminum Zirconium Tetrachlorohydrex Glycine Complex | 22.50 | 22.50 | 22.50 |
| C12–15 Alkyl Benzoate | 4.00 | 5.00 | 7.5 |
| C12–15 Alkyl Octanoate | — | 5.00 | 7.5 |
| Neopentyl Glycol Diheptanoate | 5.00 | — | — |
| PPG-1-PEG-9 Lauryl Glycol Ether | 2.00 | — | — |
| Poloxamer 105 Benzoate | — | 2.00 | — |
| PEG-8 Distearate | 2.00 | — | — |
| Stearyl Dimethicone | 0.75 | — | — |
| Polyethylene | — | 2.95 | 1.50 |
| Silica | 0.20 | 0.05 | 0.20 |
| Fragrance | 0.50 | — | — |
| Total | 100.00 | 100.00 | 100.00 |

We claim:

1. A cosmetic composition made by combining:
   (a) at least one active cosmetic material selected from the group consisting of antiperspirant active materials and deodorant active materials;
   (b) a silicone gel material which is made by combining:
      (i) a crosslinked organopolysiloxane material as a gelling agent wherein the organopolysiloxane is made from at least one silicone hydride cross-linking agent and at least one member selected from the group consisting of (A) a vinyl polysiloxane and (B) an alpha, omega diene; and
      (ii) a liquid base vehicle for the gelling agent wherein the vehicle is made by combining at least one member of the group consisting of volatile silicone materials and non-volatile silicone materials; and
   (c) at least one nonionic surfactant having an HLB value of 8–16 and an absorption time of less than 10 minutes as evaluated by testing a sample prepared by mixing (i) 95% of a mixture of 5 weight % cyclopentasiloxane cetearyl dimethicone/vinyl crosspolymer, 73.5% weight cyclomethicone and 22.5 weight % aluminum zirconium tetrachlorhydrex glycine complex as a first mixture with (ii) 5 weight % of the non-ionic surfactant as a second mixture; and
   (d) at least one emollient material selected from the group consisting of isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoate, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate. laureth-2 benzoate propylene glycol isoceteth-3 acetate, propylene glycol ceteth-3 acetate, octyldodecyl myristate, and cetyl recinoleate, myristyl myristate.

2. A cosmetic composition according to claim 1 wherein the nonionic surfactant has an HLB value of 8–12.

3. cosmetic composition according to claim 1 wherein the cosmetically active ingredient is an antiperspirant active selected from the group consisting of aluminum chlorohydrate; aluminum chloride; aluminum sesquichlorohydrate; zirconyl hydroxychloride; aluminum-zirconium glycine complex itself selected from the group consisting of aluminum zirconium trichlorohydrex gly, aluminum zirconium pentachlorohydrex gly, aluminum zirconium tetrachlorohydrex gly and aluminum zirconium octochlorohydrex gly; aluminum chlorohydrex propylene glycol; aluminum chlorohydrex polyethyleneglycol; aluminum dichlorohydrex PG; aluminum dichlorohydrex PEG; aluminum nitratohydrate and its combination with zirconyl hydroxychlorides and nitrides; and aluminum-stannous chlorohydrates.

4. A cosmetic composition according to claim 3 wherein the antiperspirant active is added to the cosmetic composition in an amount in the range of 0.1–30 percent by weight based on the total weight of the composition.

5. A cosmetic compoistion according to claim 1 which additionally comprises an antimicrobial agent selected from the group consisting of bacteriostatic quaternary ammonium compounds, cetyltrimethyl-amninomium bromide, cetyl pyridinium chloride, 2,4,4'-trichloro-2'-hydroxydiphenylether, N-(4-chlorophenyl)-N'-(3,4-dichlorophenyl)urea, silver halides, octoxyglycerin, and zinc salts.

6. A cosmetic composition according to claim 1 wherein the crosslinked organopolysiloxane material is made from at least one crosslinking agent and at least one vinyl polysiloxane.

7. A cosmetic composition according to claim 1 wherein the crosslinked organopolysiloxane material is made from at least one crosslinking agent and at least one alpha, omega diene.

8. A cosmetic composition according to claim 6 wherein the vinyl polysiloxane is selected from the group consisting of:

(a) vinyl terminated polysiloxanes of Formula I:

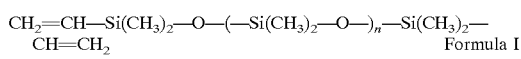
$$CH_2=CH-Si(CH_3)_2-O-(-Si(CH_3)_2-O-)_n-Si(CH_3)_2-CH=CH_2 \quad \text{Formula I}$$

(b) vinyl functional copolymers of Formula II:

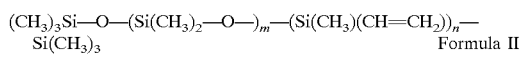
$$(CH_3)_3Si-O-(Si(CH_3)_2-O-)_m-(Si(CH_3)(CH=CH_2))_n-Si(CH_3)_3 \quad \text{Formula II}$$

where n=a number from 1–100, and m=a number from 1–100.

9. A cosmetic composition according to claim 8 wherein n=a number from 10–50.

10. A cosmetic composition according to claim 8 wherein m=a number from 10–50.

11. A cosmetic composition according to claim 8 wherein the vinyl polysiloxane comprises at least one member selected from the group consisting of:

(a) polydimethylsiloxane, which is monovinyl terminated;

(b) vinylmethyl, dimethylsiloxane copolymer which is trimethylsiloxy terminated;

(c) vinylmethyl, dimethylsiloxane copolymer which is vinyl dimethyl terminated;

(d) divinylmethyl terminated polydimethyl siloxanes;

(e) vinyl Q-resin (f) vinylphenylmethyl terminated dimethyl siloxanes;

(g) cyclicvinylmethyl dimethyl siloxanes;

(h) T-structure polydimethyl siloxanes with vinyl at branchpoint;

(i) T-structure polydimethyl siloxane with vinyl at branch terminus;

(j) diphenyl dimethyl copolymer which is vinyl terminated;

(k) vinyl terminated polydimethyl siloxanes;

(l) vinyl terminated trifluoropropyl methyl siloxane-dimethylsiloxane copolymer;

(m) vinyl terminated diethyl siloxane copolymer;

(n) vinyl methyl siloxane-dimethyl siloxane copolymer which is trimethylsiloxy terminated;

(o) vinyl gums; and (p) vinyl methyl siloxane homopolymers.

12. A cosmetic composition according to claim 7 wherein the alpha, omega diene is selected from the group consisting of Formula: $CH_2=CH(CH_2)_xCH=CH_2$, where x is a number in the range of 1–20.

13. A cosmetic composition according to claim 7 wherein the alpha, omega diene is selected from the group consisting of 1,4-pentadiene; 1,5-hexadiene; 1,6-heptadiene; 1,7-octadiene; 1,8-nonadiene; 1,11-dodecadiene; 1,13-tetradecadiene; and 1,19-eicosadiene.

14. A cosmetic composition according to claim 1 wherein the crosslinking agent is at least one member selected from the group consisting of hydride terminated polydimethylsiloxanes of Formula III:

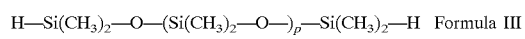
$$H-Si(CH_3)_2-O-(Si(CH_3)_2-O-)_p-Si(CH_3)_2-H \quad \text{Formula III}$$

where p=a number from 1–50.

15. A cosmetic composition according to claim 14 wherein p=a number from 5–20.

16. A cosmetic composition according to claim 1 wherein the cross-linking agent is at least one member selected from the group consisting of (a) methylhydro-dimethylsiloxane copolymer with 20–60% methyl hydrogen;

(b) methylhydrosiloxane-dimethylsiloxane copolymer;

(c) polymethylhydrosiloxanes;

(d) polyethylhydrosilane;

(e) polyphenyl-(dimethylhydrosiloxy)siloxane which is hydride terminated;

(f) methylhydrosiloxane-phenylmethylsiloxane copolymer which is hydride terminated; and (g) methylhydrosiloxane-octylmethylsiloxane copolymer.

17. A cosmetic composition according to claim 1 wherein the volatile and non-volatile silicone materials are selected from the group consisting of cyclic and linear volatile and non-volatile silicones.

18. A cosmetic composition according to claim 17 wherein the volatile silicones are one or more members selected from the group consisting of cyclic polydimethylsiloxanes represented by Formula IV:

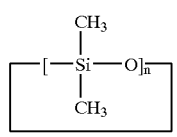

Formula IV where n is an integer with a value of 3–7.

19. A cosmetic composition according to claim 17 wherein the nonvolatile and volatile linear silicones are one or more members selected from the group consisting of linear polydimethylsiloxanes represented by Formula V:

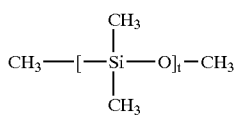

Formula V wherein "t" is selected so that molecular weight is in the range of 800–260,000 and viscosity is in the range of 5–600,000 centistokes.

20. A cosmetic composition according to claim 1 wherein the nonionic surfactant is at least one member selected from the group consisting of:
(a) sorbitan esters and ethoxylated sorbitan esters selected from the group consisting of polysorbate-20, polysorbate-40, polysorbate-60, polysorbate-80, polysorbate 120 and PEG-20 sorbitan beeswax;
(b) ethoxylates selected from the group consisting of Ceteth-20, PEG-30 castor oil, PEG-40 hydrogenated castor oil, PEG-60 hydrogenated castor oil, Ceteareth-12 Ceteareth-20, PPG-5-Ceteth-20, PPG-3-Buteth-5, Steareth-2, Steareth-10, Steareth-20, Steareth-21, Oleth-5, Oleth-9 Oleth-10 and Oleth-20;
(c) ethoxylated adducts selected from the group consisting of PEG-25 stearate;
(d) PEG esters selected from the group consisting of PEG-8 oleate, PEG-8 laurate, PEG-8 dilaurate, PEG-12 dilaurate, PEG-8 distearate, PEG-8 distearate, and PEG-40 stearate;
(e) propoxylates selected from the group consisting of PPG-10 butanediol, PPG-1-PEG-9 Lauryl Glycol Ether where PPG indicates polypropylene glycol;
(f) alkylphenol aromatic ethoxylates selected from the group consisting of dinonylphenol ethoxylated with 9 moles of ethylene oxide;
(g) block copolymers selected from the group consisting of Poloxamer 182 and Poloxamer 234;
(h) silicone polyethers selected from the group consisting of polydimethicone copolyol, dimethicone copolyol eugeno dimethicone copolyol, dimethicone copolyol isostearate, and dimethicone copolyol laurate. total weight of the silicone gel material.

21. A cosmtic composition according to claim 1 made by forming the silicone gel material with 1–30% by weight of at least one cross-linked organopolysiloxane material and 70–99% by weight of the vehicle, based on the total weight of the silicone gel material.

22. A cosmetic composition according to claim 1 made with 0.1–20% surfactant based on the total weight of the composition.

23. A cosmetic composition according to claim 1 made by combining 10–80% silicone gel material; 0.1–30% antiperspirant active; 0.1–20% surfactant wherein percents are by weight based on the total weight of the composition.

24. A cosmetic composition according to claim 23 awherein the vehicle is made by combining at least one silicone material with 0.5–50% of at least one emollient material based on the total weight of the composition.

25. A cosmetic composition according to claim 1 made by combining 0.5–10%. silicone gelling agent; 30–70% vehicle for the gelling agent; 8–25% antiperspirant active; 0.5–10% surfactant, 1–15% emollient material selected from the group consisting of hydrocarbons, fatty acid esters and silicone materials wherein a portion of the emollient material may optionally be used to form the vehicle; 0.05–5.0% fragrance; and at least one thickener selected from the group consisting of (a) 10–25% of stearyl alcohol, isostearyl alcohol, cetyl alcohol, silicone waxes, hydrogenated castor oil and mixtures thereof; and (b) 0. 1–5% of silica, cellulose, polyethylene and mixtures thereof wherein percents are by weight based on the total weight of the composition.

26. A cosmetic composition according to claim 1 made by combining: 0.5–10% silicone gelling agent; 40–80% vehicle for gelling agent; 8–25% antiperspirant active; 1–15% emollient materials selected from the group consisting of hydrocarbons, fatty acid esters and silicone materials wherein a portion of the emollient material may optionally be used to form the vehicle; 1–8% nonionic surfactant; 0.05–5.0 % fragrance and at least one thickener selected from the group consisting of (a) 1–15% of stearyl alcohol, isostearyl alcohol, cetyl alcohol, silicone waxes, hydrogenated castor oil and mixtures thereof; and (b) 0.1–5% of silica, cellulose, polyethylene and mixtures thereof wherein percents are by weight based on the total weight of the composition.

27. A cosmetic composition according to claim 26 made by combining: 0.1–10% silicone gelling agent; 50–80% vehicle for gelling agent; 8–25% antiperspirant; 1–15% emollient material selected from the group consisting of hydrocarbons, fatty acid esters and silicone materials wherein a portion of the emollient material may optionally be used to form the vehicle; 1–8% surfactant; 0.05–5.0% fragrance; and at least one thickener selected from the group consisting of (a) 1–15% of stearyl alcohol, isostearyl alcohol, cetyl alcohol, silicone waxes, hydrogenated castor oil and mixtures thereof; and (b) 0.1–5% of silica, cellulose, polyethylene and mixtures thereof wherein percents are by weight based on the total weight of the composition.

28. A cosmetic composition according to any one of claim 1, 2 or 3 wherein the gel material has a rheology profile measured in terms of the ratio of the loss modulus to the storage modulus in the range of 0.001–50.

29. A cosmetic composition according to any one of claim 1, 2 or 3 wherein the gel material has a rheology profile measured in terms of the ratio of the loss modulus to the storage modulus in the range of 0.005–20.

30. A cosmetic composition according to any one of claim 1, 2 or 3 wherein the gel material has a rheology profile measured in terms of the ratio of the loss modulus the he storage modulus in the range of 0.01–10.

31. A cosmetic composition according to claim 1 wherein the absorption time of the nonionic surfactant is less than 5 minutes.

32. A cosmetic composition according to claim 31 wherein the nonionic surfactant is at least one member selected from the group consisting of:
(a) sorbitan esters and ethoxylated sorbitan esters selected from the group consisting of polysorbate-40, polysorbate-60, polysorbate 120 and PEG-20 sorbitan beeswax;
(b) ethoxylates selected from the group consisting of Ceteth-20, PEG-30 castor oil, PEG-40 hydrogenated castor oil, PEG-60 hydrogenated castor oil, Ceteareth-12, Ceteareth-20, PPG-5-Ceteth-20, PPG-3-Buteth-5, Steareth-10, Steareth-20, Oleth-5, Oleth-9 and Oleth-10;
(c) ethoxylated adducts selected from the group consisting of PEG-25 stearate;
(d) PEG esters selected from the group consisting of PEG-8 oleate, PEG-8 laurate, PEG-8 dilaurate; PEG-12-dilaurate;
(e) propoxylates selected from the group consisting of PPG-1-PEG-9 Lauryl Glycol Ether;
(f) alkylphenol aromatic ethoxylates selected from the group consisting of dinonylphenol ethoxylated with 9 moles of ethylene oxide;
(g) block copolymers selected from the group consisting of Poloxamer 234;
(h) silicone polyethers selected from the group consisting of polydimethicone copolyol, dimethicone copolyol, eugeno dimethicone copolyol, dimethicone copolyol isostearate, and dimethicone copolyol laurate.

* * * * *